United States Patent [19]

Sneider

[11] 4,340,055
[45] Jul. 20, 1982

[54] IMPREGNATED TAMPON AND METHOD OF FABRICATING SAME

[76] Inventor: Vincent R. Sneider, 3422 Hallcrest Dr. NE., Atlanta, Ga. 30319

[21] Appl. No.: 192,720

[22] Filed: Oct. 1, 1980

[51] Int. Cl.³ ............................................. A61F 13/20
[52] U.S. Cl. .................................. 128/270; 28/118
[58] Field of Search ................ 128/263, 270, 285; 28/118

[56] References Cited

U.S. PATENT DOCUMENTS

| | | | |
|---|---|---|---|
| 2,509,241 | 5/1950 | Mende | 128/270 |
| 2,739,593 | 3/1956 | McLaughlin | 128/263 |
| 3,716,430 | 2/1973 | Croon et al. | 128/270 |
| 3,731,682 | 5/1973 | Fielding . | |
| 3,884,233 | 5/1975 | Summey | 128/263 |
| 3,902,493 | 9/1975 | Baier et al. | 128/270 |
| 3,916,898 | 11/1975 | Robinson | 128/270 |
| 3,921,636 | 11/1975 | Zaffaroni | 128/270 |
| 4,186,742 | 2/1980 | Donald | 128/270 |
| 4,196,562 | 4/1980 | Hirschman | 128/270 |

*Primary Examiner*—C. Fred Rosenbaum
*Attorney, Agent, or Firm*—Ralph R. Roberts

[57] ABSTRACT

A medicated tampon is disclosed for contraception, hygienic, or like uses, including in a swab or douche applicator, along with a novel method of fabricating the medicated tampon. The tampon is made by providing a first sheet of absorbent material to form the corpus of the tampon, and overlaying the first sheet with a second overwrap sheet of non-woven material which is permeable by body fluids. In one form of the invention a medicament is deposited between the overwrap and corpus sheets. In another form of the invention, the overwrap sheet is impregnated with a medicament. The superimposed sheets then are rolled and formed into the desired shape of the tampon with the overwrap sheet on the outside thereof so that the medicament is disposed nearest the outside of the tampon when inserted into a vaginal or other anatomical cavity.

16 Claims, 5 Drawing Figures

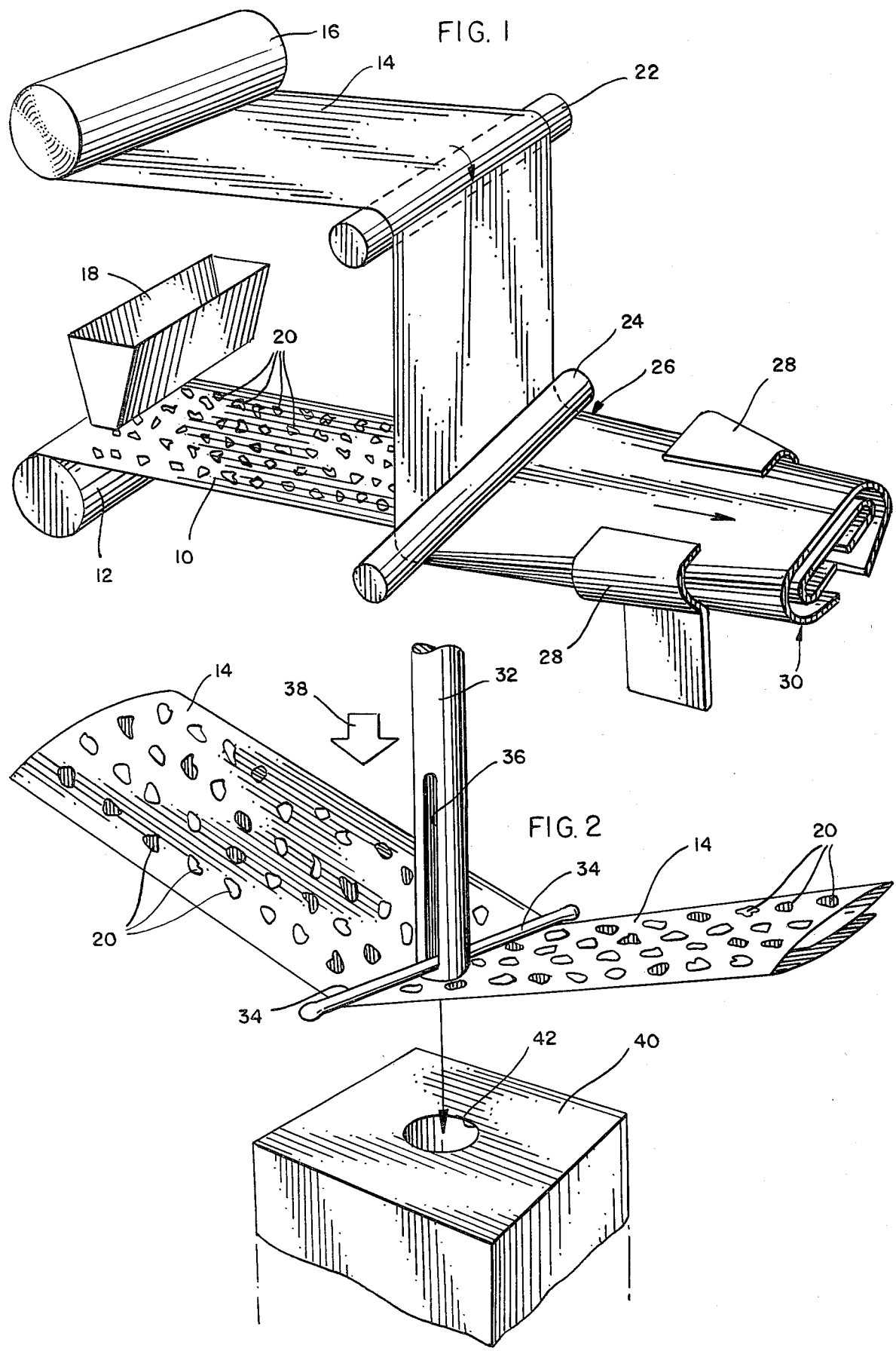

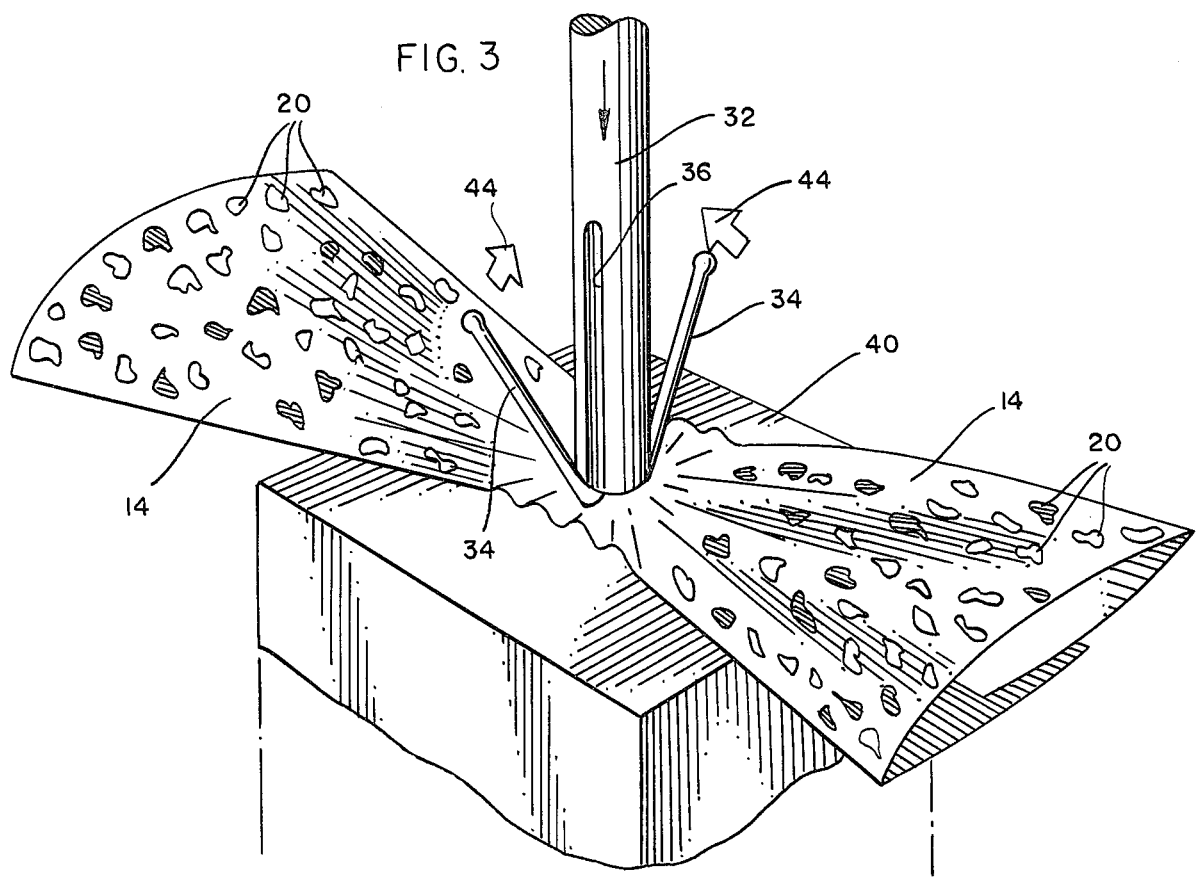
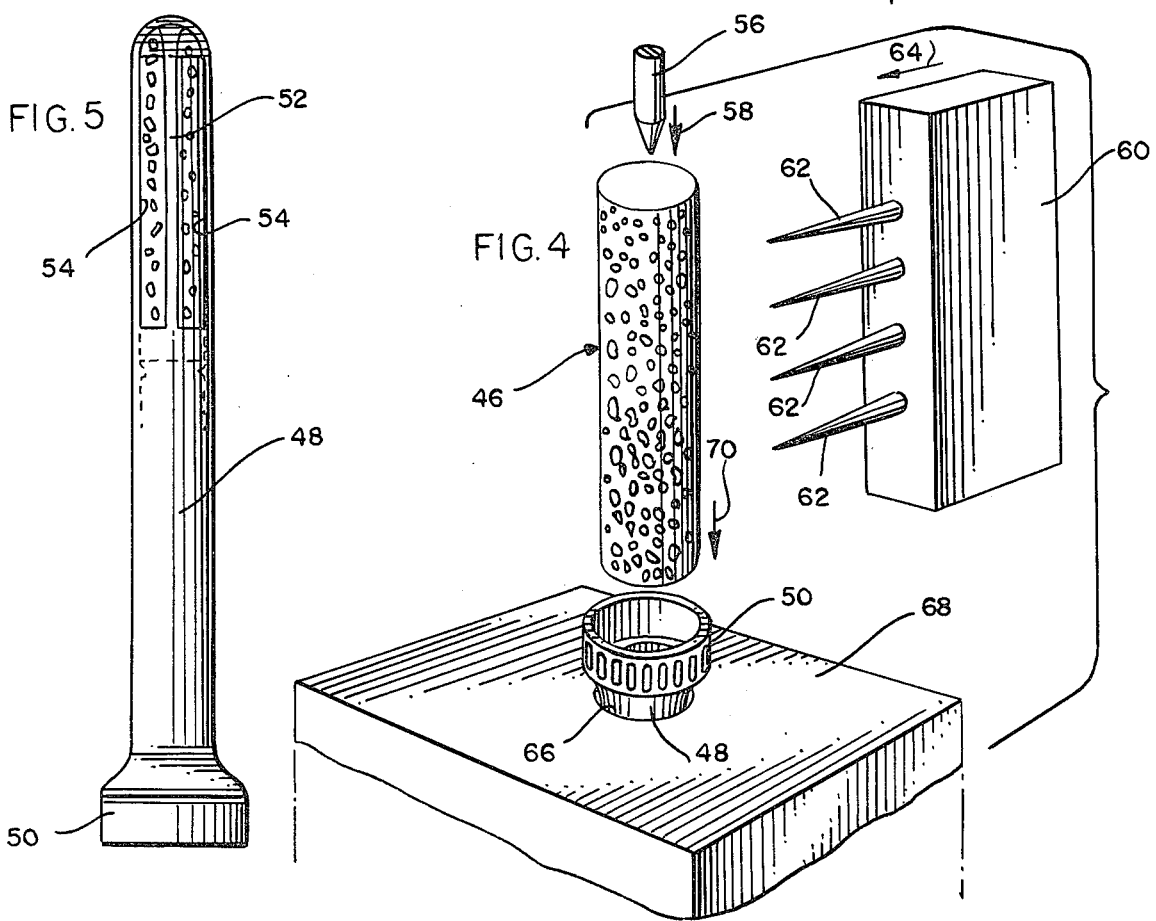

IMPREGNATED TAMPON AND METHOD OF FABRICATING SAME

BACKGROUND OF THE INVENTION

The present invention relates to a medicated tampon or drug delivery device, a method of fabricating a medicated tampon, and particularly to a tampon in a form which carries a medicament into vaginal cavities or the like.

Medicated vaginal tampons and tampon and suppository combinations are known for delivering medicaments or drugs into vaginal cavities for various reasons such as contraception or hygienic purposes. In some instances, it has become desirable to provide a means for delivering a drug into the vaginal cavity in the form of a capsule. For instance, such a tampon and drug delivery device is shown in my copending U.S. Patent Application Ser. No. 171,845, filed July 24, 1980.

In other instances, it has become desirable to provide a tampon which is impregnated or distributed with a particular solution, powdered or crystalline material. One of the problems with tampons for delivering these type of materials is that it is difficult to achieve effective activation and proper application of the medicament or drug to the walls of a vaginal cavity. In utilizing tampons for delivering medicaments and drugs, the absorbent nature of the tampon corpus itself actually inhibits the dissolving or disintegratation of the medicament or drug because the tampon itself has a tendency to absorb the body fluids rather than permitting the fluids to dissolve the medicament or drug. This is particularly true when the medicament or drug is distributed throughout the body of the tampon corpus, as well as in prior art tampons where the entire corpus itself is impregnated with the medicament or drug.

Another problem with prior art medicated tampons is in the difficulty in controlling the rate at which the medicament or drug is broken down by body fluids. With the medicament or drug distributed throughout the entire corpus of the tampon, or with the corpus impregnated throughout the entire body thereof, it is practically impossible to control the effectiveness of activation of the medicament or drug because of the differences between absorbtion of body fluids nearest the outside of the tampon versus more central portions thereof and the distance between the center of the tampon and the vaginal cavity walls.

The present invention is directed to solving the above enumerated problems by providing a medicated tampon or drug delivery device wherein the medicament or drug is maintained near the outside of the tampon when inserted into vaginal or other anatomical cavities.

SUMMARY OF THE INVENTION

An object, therefore, of the present invention is to provide a new and improved, novel medicated tampon or drug delivery device of the character described, along with a novel method of fabricating the tampon.

Another object of the invention is to provide a medicated tampon of the character described which is readily applicable for swab or douche applicators.

In the exemplary embodiment of the invention, a medicated tampon is fabricated by providing an absorbent corpus, with an overwrap about the absorbent corpus. A medicament is deposited on the overwrap so that the medicament is disposed nearest the outside of the tampon when inserted into a vaginal or other anatomical cavity. The absorbent corpus may be fabricated of cotton web or like material, and the overwrap preferably is fabricated of a non-woven material which is permeable by body fluids.

In the preferred form of the invention, the absorbent corpus material and the fluid permeable overwrap material are provided in sheet form. The sheets are superimposed and then rolled and formed into the desired shape of the tampon with the overwrap sheet on the outside thereof so that the medicament is disposed nearest the outside of the tampon.

In one form of the invention the medicament is in powdered or crystalline form and is deposited between the overwrap and corpus sheets prior to rolling and forming the sheets into the desired shape of the tampon.

In another form of the invention, the overwrap itself is impregnated with the medicament and thereby maintains the medicament nearest the outside of the tampon.

Other objects, features and advantages of the invention will be apparent from the following detailed description taken in connection with the accompanying drawings.

DESCRIPTION OF THE DRAWINGS

FIG. 1 is a perspective, somewhat schematic view of an apparatus and method of rolling and forming the corpus and overwrap sheets while depositing a medicament therebetween;

FIG. 2 is a perspective view of an apparatus illustrating an initial step of forming the rolled sheets into a desired shape for a tampon;

FIG. 3 is a view similar to that of FIG. 2 showing the apparatus sequentially forming the tampon;

FIG. 4 is a perspective view showing an apparatus for forming fluid passages in a completed formed tampon prior to assembling the tampon to an inserter means; and FIG. 5 is a side elevational view of a complete inserter and tampon assembly in the form of a douche or syringe nozzle.

DETAILED DESCRIPTION OF THE INVENTION

Referring to the drawings in greater detail, and first to FIG. 1, an apparatus and method of forming a medicated tampon from sheet material is shown. More particularly, a first sheet 10 of absorbent material is provided and rolled off of a supply roll 12 thereof. A second sheet 14 of overwrap material is provided and rolled off of a supply roll 16 thereof. Absorbent material 10 forms the corpus of the tampon and may be fabricated of cotton web or like material. Overwrap sheet 14 preferably is fabricated of non-woven material which is permeable by body fluids.

A transverse hopper 18 is provided and extends transversely across the top of corpus sheet 10 to deposit powdered or crystalline medicament or drug substances 20 on top of the sheet of absorbent corpus material 10. A pair of directional rollers 22 and 24 are provided to move the sheet of overwrap material 14 downwardly over the top of the corpus sheet 10 so that the overwrap sheet overlays or is superimposed on top of the corpus sheet in the area generally designated 26. As is apparent, at this point the medicament 20 is disposed between the overwrap and corpus sheets.

A pair of forming members 28 are provided along opposite edges of the superimposed sheets after they leave roller 24. As shown in FIG. 1, forming members 28 comprise curved and tapered flanges so that the superimposed sheets are rolled, as generally shown at 30, with the overwrap sheet on the outside of the rolled and formed composite. In this manner, the medicament 20 is disposed nearest the outside of the composite, directly underneath the non-woven overwrap sheet which is fabricated of material permeable to body fluids.

At this point, it is to be understood that the invention contemplates an impregnation of the overwrap sheet with medicaments or drugs so that when the composite is formed as described above, the desired medicament or drugs will be disposed nearest the outside of the resultant formed tampon described hereinafter.

Referring to FIG. 2, a forming plunger or rod 32 is provided with a pair of spring loaded retractable arms 34 which are biased normally toward radially outwardly extending positions as shown in FIG. 2. Forming plunger 32 is provided with an axially extending aperture 36 which opens radially outwardly for receiving arms 34 in retracted positions. Forming plunger 32 is reciprocally movable in the direction of arrow 38 toward and away from a forming die block 40 which has a central forming bore 42. The bore is dimensioned for receiving forming plunger 32 with arms 34 in their retracted positions and with the rolled and formed corpus and overlay sheets wrapped thereabout.

FIG. 3 shows forming plunger 32 in a sequential step of forcing the rolled and wrapped corpus and overlay sheets into the central forming bore of forming die block 40, with arms 34 moving upwardly in the direction of arrows 44 toward their retracted positions within aperture 36 of the forming rod. This movement continues until a properly shaped tampon is formed as indicated generally at 46 in FIG. 4.

Forming plunger 32 then is moved back out of bore 42 in forming die block 40, and spring loaded arms 34 again will move radially outwardly to their normal biased positions shown in FIG. 2 for the next forming operation. It should be noted that arms 34 are provided to maintain the corpus and overwrap sheets in a generally flat condition prior to the aforesaid forming operation and to prevent the sheet material from bunching as it is uniformly gathered into its desired shape as shown in FIG. 3. In addition, appropriate cutting means, not shown, is provided for severing the rolled sheet material as it leaves the rolling station shown in FIG. 1 and toward the forming station shown in FIGS. 2 and 3.

The formed tampon 46 then is removed from bore 42 of forming die 40, by any appropriate means, and is moved to an assembly station shown generally in FIG. 4, where the tampon is pierced to form fluid passages therethrough and then assembled to an appropriate inserter means. More particularly, reference is made to my copending U.S. Patent Application Ser. No. 176,105, entitled "Expanding Swab Applicator", filed Aug. 7, 1980, and which is incorporated herein by reference. In that application, the expanding tampon is shown assembled to and within a tubular inserter means 48 (FIG. 5) in the form of a syringe or douche nozzle having a threaded end 50 for screw assembly onto the neck of a syringe or douche container. Briefly, the nozzle includes a plurality of axially extending ribs 52 at the distal end thereof, defining axially extending slots 54 through which the expandable tampon 46 protrudes when wetted so that the tampon and nozzle combination becomes a swab applicator. The swab applicator is used for a wide range of applications, particularly for hygienic purposes.

Referring back to FIG. 4, an axially extending and reciprocal piercing rod 56 is shown in axial alignment with tampon 46. The piercing rod is reciprocal in the direction of arrow 58. In addition, a mounting block 60 is provided with radially extending piercing rods 62 which are fixed to the mounting block for reciprocal movement therewith in a radial direction as generally indicated by the arrow 64. Piercing rods 58 and 62 are provided for forming axial and radial fluid passages, respectively, through tampon 46 to facilitate better wetting thereof by fluid emanating through the interior of nozzle 48 from the appropriate douche or syringe container. More details of the fluid passages, as well as the construction of nozzle 48 can be seen by reference to my aforesaid copending application Ser. No. 176,105.

At the assembly station shown in FIG. 4, nozzle 48 is inverted and inserted into a positioning bore 66 in a holding block 68. Fluid passages then are formed in tampon 46 by axial piercing rod 56 and radial piercing rods 62 moving sequentially inwardly and outwardly toward and away from tampon 46 in the direction of arrows 58 and 64, respectively. The tampon then is inserted in the direction of arrow 70 through the threaded end 50 of nozzle 48 and into the nozzle until the tampon reaches its ultimate position at the distal end of the nozzle as shown in FIG. 5. The assembly then forms a swab applicator for a wide variety of uses as discussed in detail in my aforesaid application Ser. No. 176,105.

It should be noted that the assembly and use of tampon 46 as shown in and described in relation to FIGS. 4 and 5 is but one intended use of the novel medicated tampon of the present invention. The tampon of the present invention can be used with other applicators, and particularly can be used solely as an absorbent medicated tampon for contraception, hygienic and other purposes.

It will be understood that the invention may be embodied in other specific forms without departing from the spirit or central characteristics thereof. The present examples and embodiments, therefor, are to be considered in all respects as illustrative and not restrictive, and the invention is not to be limited to the details given herein.

I claim:

1. A method of fabricating a medicated tampon comprising the steps of:
    providing an absorbent corpus in sheet form;
    providing an overwrap in sheet form about said absorbent corpus, and
    disposing a medicament between said overwrap and the absorbent corpus and overlaying the sheets and forming said sheets into the desired shape of the tampon with the overwrap on the outside so that the medicament is disposed nearest the outside of the tampon when inserted into an anatomical cavity.

2. The method of claim 1 including providing said absorbent corpus of cotton web or like material.

3. The method of claim 1 including providing said overwrap of non-woven material permeable by body fluids.

4. The method of claim 1 including providing said medicament in crystalline form.

5. The method of claim 1 wherein said medicament is deposited on said overwrap by impregnating the overwrap with said medicament.

6. The method of claim 1 including providing said formed tampon with fluid passages therethrough for better wetting thereof.

7. A medicated tampon, comprising:
an absorbent corpus in sheet form;
an overwrap in sheet form about said corpus, said overwrap being permeable by body fluids, and
a medicament between said overwrap and the absorbent corpus, said corpus and overwrap rolled and formed into the desired shape of the tampon so that the medicament is disposed nearest the outside of the tampon when inserted into an anatomical cavity.

8. The medicated tampon of claim 7 wherein said absorbent corpus is fabricated of cotton web or like material.

9. The medicated tampon of claim 7 wherein said overwrap is fabricated of non-woven material.

10. The medicated tampon of claim 7 wherein said overwrap is impregnated with said medicament.

11. The medicated tampon of claim 7 wherein said medicament is disposed between said overwrap and said corpus.

12. The medicated tampon of claim 11 wherein said medicament is in crystalline form.

13. A method of fabricating a medicated tampon, comprising the steps of:
providing a first sheet of absorbent material to form the corpus of said tampon,
overlaying said first sheet with a second sheet of overwrap material permeable by body fluids,
depositing a medicament on said overwrap sheet, and
rolling and forming said sheets into the desired shape of the tampon with the overwrap sheet on the outside thereof so that the medicament is disposed nearest the outside of the tampon when inserted into an anatomical cavity.

14. The method of claim 13 wherein said medicament is deposited between said overwrap and said corpus.

15. The method of claim 13 including providing said medicament in crystalline form.

16. The method of claim 13 wherein said medicament is deposited on said overwrap by impregnating the overwrap with said medicament.

* * * * *